United States Patent [19]

Schneider et al.

[11] 4,421,509
[45] Dec. 20, 1983

[54] LEG BAG FOR URINARY INCONTINENCE

[75] Inventors: Barry L. Schneider, Deerfield; David V. Beddow, Lake Villa, both of Ill.

[73] Assignee: Hollister Incorporated, Libertyville, Ill.

[21] Appl. No.: 273,363

[22] Filed: Jun. 15, 1981

[51] Int. Cl.³ ............................................. A61M 1/00
[52] U.S. Cl. ..................................... 604/317; 604/327
[58] Field of Search ............................ 150/0.5, 1.0, 8; 4/144.1, 144.2, 144.3, 144.4; 128/DIG. 24, 295, 275, 760, 762, 767, 283; 222/530, 536; 604/317, 322, 327, 328, 329, 349

[56] References Cited

U.S. PATENT DOCUMENTS

| Re. 30,607 | 3/1981 | Manschot et al. | 128/762 |
|---|---|---|---|
| 2,883,985 | 4/1959 | Evans | 604/327 |
| 2,928,393 | 3/1960 | Marsan | 128/283 |
| 3,564,620 | 2/1971 | Clark | 4/110 |
| 3,897,780 | 8/1975 | Trousil | 128/295 |
| 4,073,295 | 2/1978 | Laufbahn | 128/295 |
| 4,173,979 | 11/1979 | Odis | 128/295 |
| 4,305,290 | 12/1981 | Taylor | 128/762 |

OTHER PUBLICATIONS

Photocopy of Model "Uri-Drain" Reorder 5-7331 Chesebrough-Ponds, Greenwich, Conn. 06830.

Primary Examiner—C. Fred Rosenbaum
Assistant Examiner—J. L. Kruter
Attorney, Agent, or Firm—Tilton, Fallon, Lungmus

[57] ABSTRACT

An expandable plastic collection bag adapted to be strapped to the leg of an incontinent patient and provided with an inlet tube for directing urine into the bag. The bag also has a clamp-equipped discharge tube to facilitate periodic draining of the bag's contents. The straps are located to exert a force urging the inner wall of the bag into conforming engagement with a wearer's leg, and side pleats allow expansion of the bag in a way that permits a relatively large portion of the inner wall to remain in surface contact with the leg. The inlet and outlet tubes are hingedly mounted for self-adjusting limited pivotal movement towards and away from the bag's outer wall to reduce possibilities that the flow passages might become kinked as the bag is filled. Such pivotal movement is facilitated by openings and by heat seal lines formed in the walls of the bag at the locations of the inlet and outlet tubes. Upper and lower sections of the bag are disposed between the respective inlet and outlet tubes and the wearer to shield the wearer's leg against direct contact with such tubes, and a pocket is provided adjacent the inlet tube (and also, if desired, adjacent the outlet tube) to receive and protect the tube against contamination during handling and storage of the bag.

22 Claims, 6 Drawing Figures

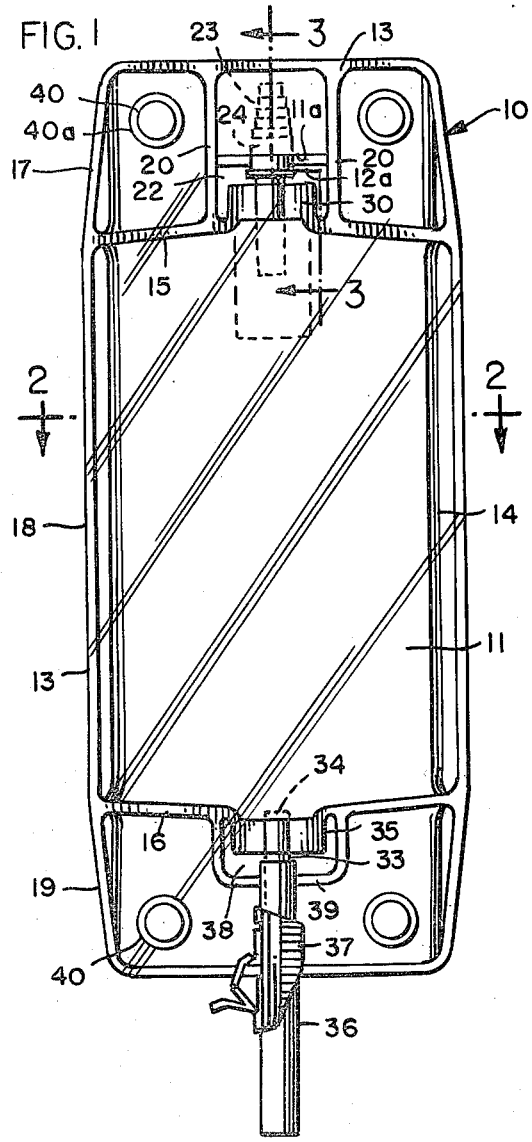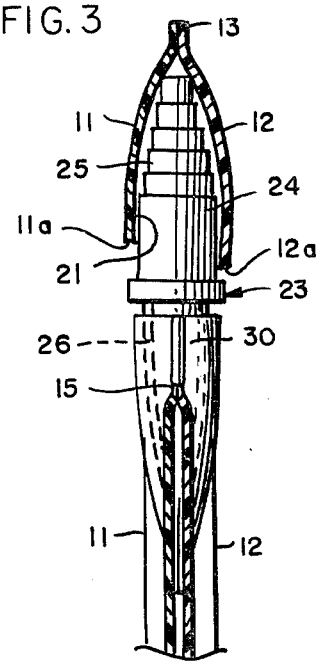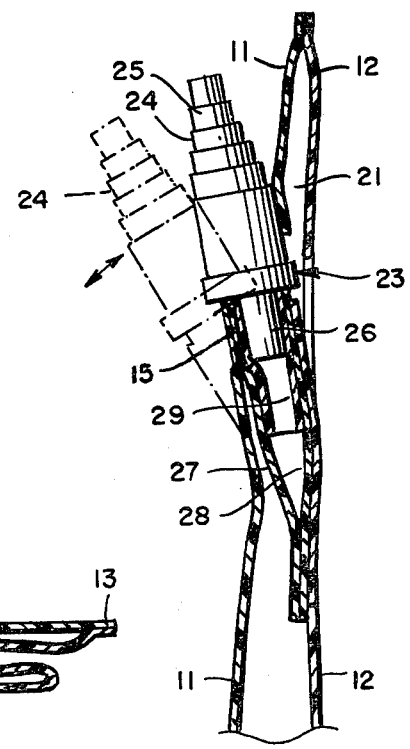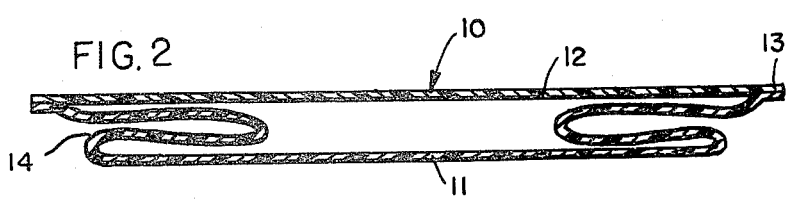

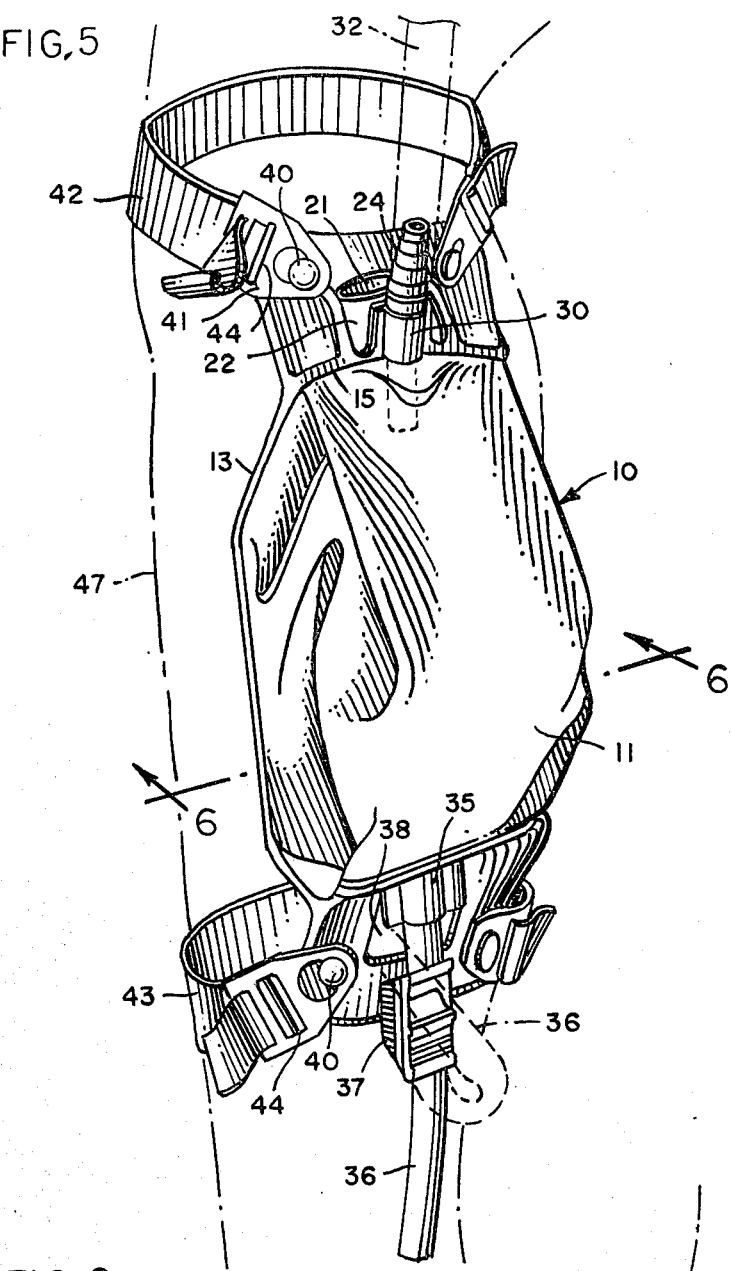
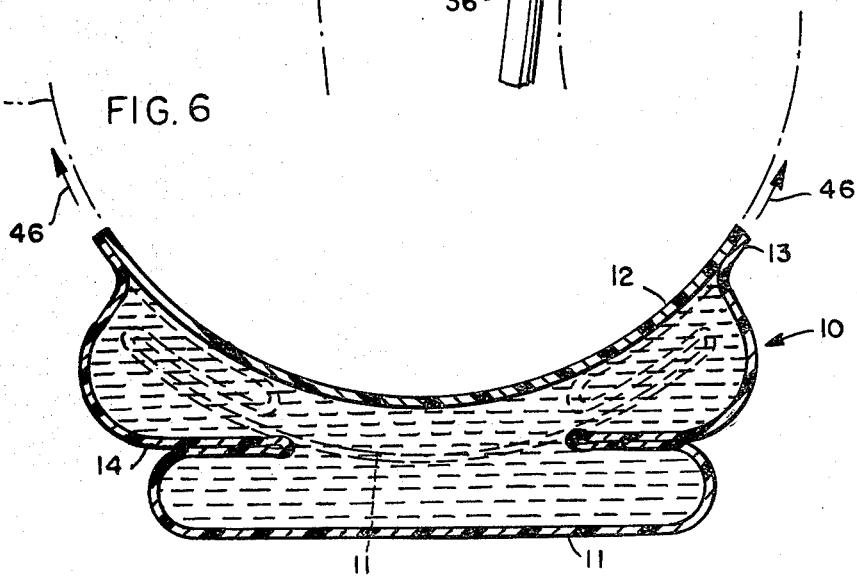

LEG BAG FOR URINARY INCONTINENCE

BACKGROUND AND SUMMARY

Leg bags now in use by patients suffering from urinary incontinence are commonly equipped with inlet and outlet tubes and are designed to be strapped to a patient's leg for receiving urine directed thereto by a suitable catheter or collection tube. Because of the extended periods over which such bags are worn, it is important that contact forces be distributed as evenly as possible to avoid the development of sores, abrasions, and ulcers, and to promote greater patient comfort. Such bags should also be easy to attach, detach, and operate, be non-refluxing, non-kinking, and leak-proof in use, and be easy to connect to a sterile catheter, such as an indwelling catheter, without contaminating the flow system.

Currently-available bags are at best only partially effective at meeting these requirements. Often such bags tend to buckle in use, creating pressure points against a wearer's leg and increasing the possibilities of kinking, obstruction, backflow, disconnection, and/or rupture of the bag. Upon filling, such bags may expand in a direction away from the wearer's leg, greatly reducing the area of leg contact and increasing the force per area to create pressure points or zones. In some cases, nozzles and clamps are exposed for direct contact with the wearer's leg, not only producing discomfort but also increasing the possible development of pressure sores or ulcers. Finally, although at least some of the commercially-available bags are marketed in sterile condition with removal caps over the inlet and outlet tubes, such caps are easily dislodged and misplaced and, if prematurely removed, may expose the tubes to contamination.

A main object of this invention is to provide an improved leg bag which overcomes these shortcomings of prior bag constructions. Specifically, the bag is constructed to maximize the area of leg contact even when the bag is expanded in use, to avoid the development of pressure points or zones, to prevent direct contact between the bag's inlet and outlet tubes and the wearer's leg, to allow limited pivotal movement of such tubes, to provide a construction in which the hinged tubes tend to pivot automatically as the bag is filled to maintain positions generally parallel with the wearer's leg, thereby reducing the possibilities of kinking and flow obstruction in use and to provide a simple but highly effective means for protecting the inlet tube and, if desired, the outlet tube, against contamination, even if the sterile bag should contact a non-sterile surface or object upon removal from its wrapper.

Briefly, the bag is generally flat (when unexpanded), vertically elongated, and formed of flexible thermoplastic sheet material. Straps are provided for securing the bag to a patient's leg. Such straps are connected to upper and lower sections of the bag so that when fitted about a patient's leg they tend to urge the inner or rear wall of the bag into conforming engagement with the leg. As the bag is filled in use, side pleats formed in the outer wall of the bag expand to accommodate the fluid in a way that permits a relatively large area of the inner wall to remain in contact with the patient's leg, particularly in the portion of the bag in which the fluid is retained. The sizable area of contact promotes security and patient comfort, and reduces the possibilities that localized pressures might create irritations and produce sores.

The inlet and outlet assemblies of the bag are hingedly mounted for self-adjusting pivotal movement in use. As the bag expands, the outer wall bulges outwardly. The hinged mounting of the upper and lower tube assemblies permits those assemblies to remain parallel with the wearer's leg and to resist the angulation which such outward bulging of the bag might otherwise produce. Because the tubes are allowed to remain parallel with the leg, the possibilities of pressure point development and the chances that the flexible tube or catheter leading to the inlet tube might become kinked in use, are further reduced. U-shaped openings adjacent the inlet and outlet tubes, and transverse heat seal lines at those locations, facilitate the self-adjusting pivotal movement of the tube assemblies.

The upper and lower sections of the bag shield the wearer against direct contact with the inlet and outlet tubes, against helping to avoid the development of skin irritations and sores. Such upper and lower sections may be provided with pockets for receiving the inlet and/or outlet tubes and protecting such tubes against contamination prior to use or during storage following use.

Other features, objects, and advantages of the invention will become apparent from the specification and drawings.

DRAWINGS

FIG. 1 is a front or outer view illustrating the bag in the generally vertical position it would be oriented in normal use.

FIG. 2 is an enlarged horizontal sectional view taken along line 2—2 of FIG. 1.

FIG. 3 is an enlarged vertical sectional view taken along line 3—3 of FIG. 1.

FIG. 4 is a sectional view similar to FIG. 3 but illustrating the inlet tube removed from its protective pocket.

FIG. 5 is a perspective view illustrating the bag in a position of use and in partially-filled condition.

FIG. 6 is a somewhat schematic sectional view taken along line 6—6 of FIG. 5.

DETAILED DECRIPTION

Referring to the drawings, the numeral 10 designates a leg bag of generally rectangular outline formed of any flexible fluid impervious thermoplastic material. Polyvinyl chloride has been found particularly effective but other thermoplastics such as polyolefins may be used. The bag is generally flat when uninflated, having an outer or front wall 11 and a generally parallel inner or rear wall 12 joined together by peripheral heat sealing line 13. As shown most clearly in FIG. 2, the outer or front wall 11 has accordion-folded side portions 14 which are adapted to unfold outwardly as the bag is filled. The folds extend the full vertical extent of the bag, but upper and lower transverse heat seal lines 15 and 16 fuse the material of the folds to that of the inner and outer walls, thereby obliterating the folds along such transverse lines. Lines 15 and 16 effectively divide the bag into an upper section 17, a central body section 18, and a lower section 19. The upper section has an additional pair of longitudinally-extending parallel heat seal lines 20 which, together with line 13 at the bag's upper end, define the sealed edges of a downwardly-facing pocket 21. Directly below the pocket, the inner and outer walls of the bag are cut away to define an aperture 22, and an inlet tube assembly 23 is secured to the bag within that aperture, or along the lower limits thereof, and communicates with the interior of central section 18.

The inlet tube assembly 23 includes a relatively rigid plastic inlet nozzle 24 having a stepped upwardly-facing end portion 25 and a reduced lower end portion 26. A pair of vinyl panels 27 and 28 are sealed to a sleeve 29 secured to the lower tubular portion 26 of the inlet nozzle and extend below the end of that nozzle to form a normally-closed flap or flutter valve. The one-way valve allows fluid to enter the interior of the central section 18 but prevents refluxing or reverse flow, as well known in the art. Sleeve 28 is formed of resilient plastic and projects downwardly from lower portion 26 to distribute forces applied to panel 28 of the flap valve and to inner wall 12 of the bag when the nozzle assembly is pivoted outwardly about transverse hinge line 15 as shown by solid and broken lines in FIG. 4.

The lower portion 26 of the nozzle, the panels 27 and 28 of the flap valve, and the sleeve 29 are heat sealed or otherwise permanently secured within neck portion 30 within upper aperture 22. Neck portion 30 is composed of upward extensions of the inner and outer walls of central section 18 that are not only heat sealed to each other but also to the inlet tube assembly 23.

It will be observed from the drawings that the upper end of inlet nozzle 24 terminates below the upper limits of the bag. By simply deforming the material of the bag, the upper portion 25 of the nozzle may be easily inserted into, and removed from, pocket 21 (FIGS. 1, 3). The bag would ordinarily be supplied to the purchaser in sterile condition with nozzle 24 protected within pocket 21; hence, even if the bag, following its removal from a sterile wrapper (not shown), is brought into contact with non-sterile surfaces or is handled by a user who is not wearing sterile gloves, the upper portion of the nozzle should be protected against contamination as long as it remains shielded within pocket 21. When the bag is to be used, the nozzle is easily extracted from the pocket and a flexible catheter or drainage tube 32 (FIG. 5) is slipped over the stepped end portion 25. If, following a period of use, the bag is to be rinsed, dried, and stored for re-use, the nozzle may be reinserted into the pocket to protect the nozzle during storage. The pocket may therefore function during later use as a dust cover as well as initially as a sterility protector. Ideally, to facilitate insertion and removal of the nozzle from pocket 21, the lower front edge 11a of the pocket's mouth should be spaced above the lower rear edge 12 of that mouth (FIGS. 1 and 3).

An outlet tube assembly 33 communicates with the interior of the central body section 18 at the lower end of the section. The assembly includes a short outlet tube 34 heat sealed to downwardly-extending neck portion 35 below transverse heat seal line 16. A drain tube 36 of soft latex or other suitable material may be fitted over the outlet tube 34 and form an extension thereof. A shut-off clamp 37 is carried by the drain tube 36 and may be easily manipulated to fully open or fully close the passage of that tube.

An aperture 38, formed by aligned cut-outs in the inner and outer walls of the bag in the vicinity of neck 35, is similar to aperture 22 already described. Heat seal line 39 is shown to be generally U-shaped and, hence, no lower pocket is provided beneath aperture 38. It is to be understood, however, that a pocket similar to pocket 21 may be provided to receive the drainage tube 36 and clamp 37. Such a pocket would have the advantage of preventing flopping movement of tube 36 and would prevent or reduce direct contact between the tube and the wearer's leg. To the extent that the drainage tube 36 would be kinked or folded in order to be received in such a pocket, additional insurance against leakage would be provided.

Even where no lower pocket is provided, it has been found that the flexible and readily deformable outlet tube 36 may be easily kinked and its free end may be inserted upwardly into the U-shaped aperture 38, as shown in broken lines in FIG. 5.

The upper and lower corners of the bag 10 are provided with resilient buttons 40 projecting outwardly from the outer walls of the upper and lower sections 17 and 19, respectively. The buttons may be formed from the same material (such as polyvinyl chloride) as the remainder of the bag and are fused or heat sealed to the walls of the upper and lower sections. Therefore, in the area immediately surrounding each button, the outer and inner walls 11, 12 of the bag are sealed to each other as well as to the button. Despite the annular heat seal 40a securing each button in place, the rear surface of the inner panel is substantially smooth or flush with the surrounding surface of wall 12.

The buttons are received by plastic buckles 41 of upper and lower straps 42 and 43, respectively (FIG. 5). Adjoining openings in each buckle allow the buckle to be detached from button 40. The ends of each strap are threaded through slots 44 in each buckle in a way that locks the strap in place but at the same time permits adjustment of strap length and tensioning at will, all as well known in the art. For greater patient comfort and security, straps 42 and 43 are preferably formed of an elasticized fabric—that is, a fabric having elastic threads which impart stretchability but also having non-elastic threads that limit the extent of the stretching action.

FIG. 5 illustrates the bag 10 supported on the inside of a patient's lower leg. The bag is depicted in substantially filled condition to reveal the changes in its shape that occur under conditions of use. When empty, the bag generally follows the contour of a wearer's leg as schematically indicated in broken lines in FIG. 6. Straps 42 and 43 exert lateral tensioning forces in the directions indicated by arrows 46, thereby urging the inner wall 12 of the bag into contact with leg 47 and, in so doing, imposing a horizontal curvature on the inner wall. As the bag fills, the curvature of the inner wall tends to remain because of the tensioning forces and because side pleats 14 unfold or revert to allow bag expansion without an objectionable pulling away from the leg of that portion of the inner wall 12 of the bag in which the liquid contents are carried (FIG. 6). The result is a construction which maintains a substantial surface area of contact even when the bag is filled, thereby reducing the possibility that pressure points might develop and cause discomfort or injury to the patient.

The fact that the upper and lower nozzle tubes 24 and 33 are disposed along the outer sides of upper and lower bag sections 17 and 19, and are thereby shielded against direct contact with the patient by those sections, also reduces the possibilities that pressure points and patient injury might result. U-shaped apertures 22 and 38 are particularly important because they allow outward limited pivotal movement of the upper and lower tube assemblies along transverse hinge lines 15 and 16. As shown in FIG. 5, the upper and lower apertures allow the nozzles of the filled (or partially filled) bag to pivot outwardly and thereby maintain positions generally parallel with the surface of the wearer's leg. The possibility that the soft inlet tube 32 might become kinked in use is therefore greatly reduced.

While in the foregoing we have disclosed an embodiment of the invention in considerable detail for purposes of illustration, it will be understood by those skilled in the art that many of these details may be varied without departing from the spirit and scope of the invention.

We claim:

1. A generally flat, elongated, expandable bag formed of flexible thermoplastic material and adapted to be secured to a patient's leg for the collection of urine with the longitudinal axis of said elongated bag normally disposed vertically; said bag having inner and outer walls that are peripherally joined together and are generally parallel when the bag is empty; said bag also having upper, central, and lower sections; said inner and outer walls being provided with aligned openings together defining an aperture extending through said upper section immediately above said central section and being sealed together along a transverse seal line across said bag and defining the lower limits of said aperture; an inlet tube secured to said bag along said transverse seal line and communicating with the interior of said central section below said aperture; said inlet tube including an elongated inlet nozzle projecting upwardly into and beyond said aperture and overlying the outer wall of said upper section; said inlet nozzle being adapted for connection to a urinary drainage tube; and a pair of laterally-spaced fasteners provided by each of said upper and lower sections; said pair of fasteners of said upper section being located above said transverse seal line.

2. The bag of claim 1 in which said aperture and said inlet nozzle are located along the longitudinal axis of said bag.

3. The bag of claim 2 in which said inlet nozzle is formed of rigid plastic material.

4. The bag of claim 1 in which said transverse seal line comprises a heat seal line extending generally horizontally across said bag and isolating the interior of said central section from that of said upper section.

5. The bag of claim 4 in which said heat seal line forms a hinge for outward and inward pivotal movement of said inlet nozzle.

6. The bag of claim 1 in which said outer wall is reversely folded along its vertical side edges to define accordion-folded side wall portions adapted to unfold as said bag is filled.

7. The bag of claim 1 in which said inner and outer walls of said upper section above said aperture defines a downwardly-opening pocket for receiving and protecting said inlet nozzle; said nozzle being removable from said pocket when use of said bag is desired.

8. The bag of claim 1 in which said inner and outer walls are provided with a second pair of aligned openings together defining a second aperture located in said lower section immediately below said central section; said inner and outer walls being sealed together along a second transverse seal line extending across said bag and defining the upper limits of said second aperture; an outlet tube secured to said bag along said second transverse seal line and communicating with said central section above said second aperture; said outlet tube including a flexible drain tube projecting downwardly beyond said second aperture and over the outer wall of said lower section; said pair of fasteners of said lower section being located below said second transverse seal line.

9. The bag of claim 8 in which said second aperture and said outlet tube are located along the vertical midline of said bag.

10. The bag of claim 8 in which said second-mentioned transverse seal line extends general horizontally across said bag and isolates the interior of said central section from that of said lower section.

11. The bag of claim 10 in which said second transverse seal line is a heat seal line and forms a hinge for outward and inward pivotal movement of said outlet tube.

12. The bag of claim 8 in which a shut-off clamp is supported on said flexible drain tube.

13. The bag of claims 1 or 8 in which strap means are detachably engagable with each pair of said fasteners for retaining said bag in place upon a wearer's leg and for laterally tensioning said upper and lower sections of the bag when so retained.

14. The bag of claim 8 in which said inner and outer walls of said lower section below said second aperture define an upwardly-facing pocket for receiving said drain tube.

15. A generally flat, elongated, expandable bag formed of flexible thermoplastic material and adapted to be secured to a patient's leg for the collection of urine with the longitudinal axis of said elongated bag normally disposed vertically; said bag having inner and outer walls that are peripherally joined together; said walls being generally parallel when the bag is empty and having upper, central, and lower sections; said central section being delineated from said upper and lower sections by transversely-extending upper and lower heat seal lines; said inner and outer walls being provided with aligned openings together defining an aperture extending through said upper section immediately above said central section; an inlet tube disposed along the outer side of said bag and communicating with the interior of said central section at a point adjacent the upper heat seal line; an outlet tube assembly disposed along said outer wall and communicating with the interior of said central section at a point adjacent the lower heat seal line; said outer wall being reversely folded along its vertical sides to define accordion-folded side wall portions adapted to unfold as said bag is filled; the accordion folds of each side wall portion being heat sealed to each other and to said inner wall by said upper and lower transversely-extending heat seal lines; said inlet tube being adapted for connection to a urinary drainage tube; said inlet tube including an inlet nozzle projecting upwardly into and beyond said aperture and normally overlying the outer wall of said upper section.

16. The bag of claim 15 in which said inlet and outlet tubes are located along the longitudinal axis of said bag.

17. The bag of claim 15 in which said aperture is of inverted u-shaped configuration.

18. The bag of claim 15 in which said upper section provides a downwardly-facing pocket for removably receiving and protecting said inlet tube.

19. The bag of claim 15 in which said inner and outer walls of said lower section are provided with aligned openings together defining a second aperture extending through said lower section immediately below said central section; said outlet tube projecting downwardly into and beyond said second aperture and normally overlying said outer wall of said lower section.

20. The bag of claim 19 in which said aperture is of U-shaped configuration.

21. The bag of claim 19 in which said lower section is provided with an upwardly-facing pocket for removably receiving and protecting said outlet tube.

22. The bag of claim 15 in which a pair of laterally-spaced fasteners is provided by each of said upper and lower sections; and strap means are detachably engagable with each pair of said fasteners for retaining said bag in place upon a wearer's leg and for laterally tensioning said upper and lower sections of the bag when so retained.

* * * * *